US012558507B2

(12) United States Patent

Luo

(10) Patent No.: US 12,558,507 B2

(45) Date of Patent: *Feb. 24, 2026

(54) RESPIRATORY MASK WITH SPONGE AND FABRIC

(71) Applicant: DCSTAR INC., New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/081,772

(22) Filed: Mar. 17, 2025

(65) Prior Publication Data

US 2025/0213811 A1 Jul. 3, 2025

Related U.S. Application Data

(63) Continuation of application No. 18/509,937, filed on Nov. 15, 2023, now Pat. No. 12,274,829.

(51) Int. Cl.
*A61M 16/06* (2006.01)

(52) U.S. Cl.
CPC . *A61M 16/0622* (2014.02); *A61M 2205/0216* (2013.01)

(58) Field of Classification Search
CPC ... A61F 13/2002; A61F 5/00; A61K 2800/10; A61K 2800/54; A61K 8/0208; A61K 8/895; A61L 31/06; A61L 31/10; A61L 31/146; A61M 16/0057; A61M 16/024; A61M 16/06; A61M 16/0605; A61M 16/0611; A61M 16/0616; A61M 16/0622; A61M 16/0633; A61M 16/0666; A61M 16/0683; A61M 16/0688; A61M 16/0816; A61M 16/0825; A61M 16/0858; A61M 16/0875; A61M 16/16; A61M 16/209; A61M 2016/0661; A61M 2202/0007; A61M 2202/0085; A61M 2202/0208; A61M 2202/0225; A61M 2205/02; A61M 2205/0205; A61M 2205/0216; A61M 2205/0222; A61M 2205/0238;

(Continued)

(56) References Cited

U.S. PATENT DOCUMENTS

| | | | | | |
|---|---|---|---|---|---|
| 3,815,596 | A | * | 6/1974 | Keener | ............. A61M 16/0833 128/205.25 |
| 5,243,971 | A | * | 9/1993 | Sullivan | ................ A61M 16/06 128/207.18 |

(Continued)

*Primary Examiner* — Annette Dixon

(74) *Attorney, Agent, or Firm* — HSML P.C.

(57) ABSTRACT

A respiratory mask configured to adapt and comfortably seal according to the facial features of different users. The respiratory mask includes a support chamber, a cushioning part, and a comfort layer. The support chamber has curved sidewalls and two circular openings of varying sizes. The cushioning part includes of an elastic body and a sponge body. The fixed side of the elastic body is connected to the support chamber. The sponge body has a curved side and a connecting side that connects to the elastic body. The first side of the comfort layer is configured to make partial contact with the user's face, while the second side of the comfort layer connects to the sponge body. Both the cushioning part and the comfort layer are configured to deform, collaboratively ensuring a tight seal around the user's face.

20 Claims, 10 Drawing Sheets

(58) Field of Classification Search
   CPC ...... A61M 2205/276; A61M 2205/583; A61M
              2205/59; A61M 2207/00; A61M 2207/10;
              A61M 2209/06; A61M 2210/0618; A61M
              2210/0625; A61Q 19/00; B33Y 80/00;
              C08G 77/12; C08G 77/392; C08L 83/08
   See application file for complete search history.

(56)                    References Cited

U.S. PATENT DOCUMENTS

| | | | | |
|---|---|---|---|---|
| 5,484,645 | A * | 1/1996 | Lickfield | D04H 3/14 |
| | | | | 428/374 |
| 11,110,241 | B2 | 9/2021 | Lockhart et al. | |
| 11,260,193 | B2 | 3/2022 | Guney et al. | |
| 12,274,829 | B1 * | 4/2025 | Luo | A61M 16/0622 |
| 2003/0145859 | A1 * | 8/2003 | Bohn | A61M 16/06 |
| | | | | 128/206.28 |
| 2009/0308404 | A1 | 12/2009 | Leonard et al. | |
| 2012/0204881 | A1 * | 8/2012 | Davidson | A61M 16/0605 |
| | | | | 128/206.25 |
| 2014/0109911 | A1 | 4/2014 | Asvadi et al. | |
| 2014/0251338 | A1 * | 9/2014 | Asvadi | C08G 77/392 |
| | | | | 128/206.22 |
| 2022/0096769 | A1 | 3/2022 | Guney et al. | |

* cited by examiner

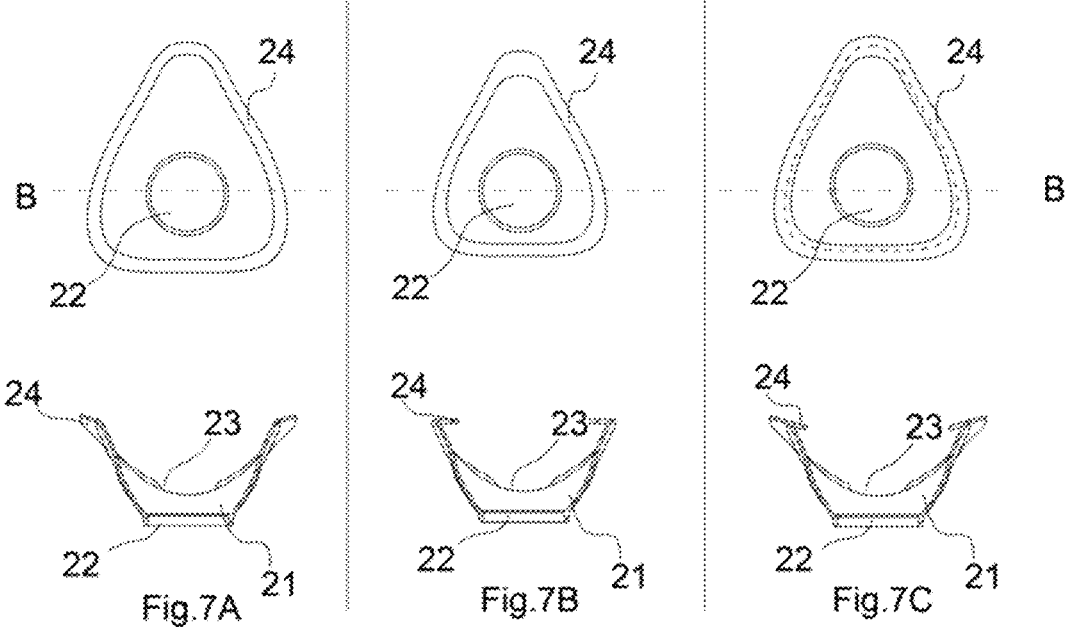
Fig.7A          Fig.7B          Fig.7C
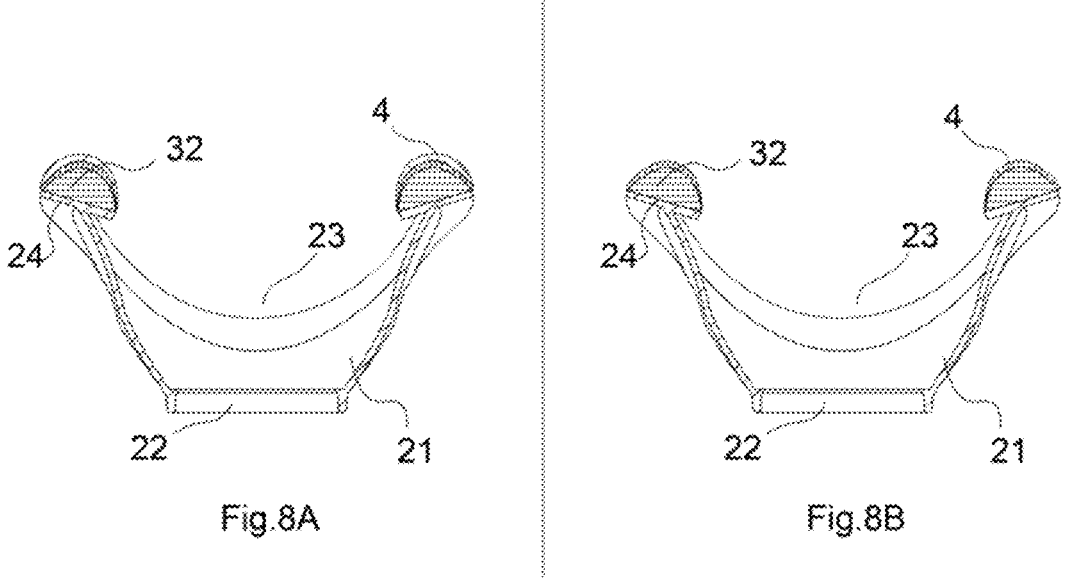
Fig.8A                    Fig.8B

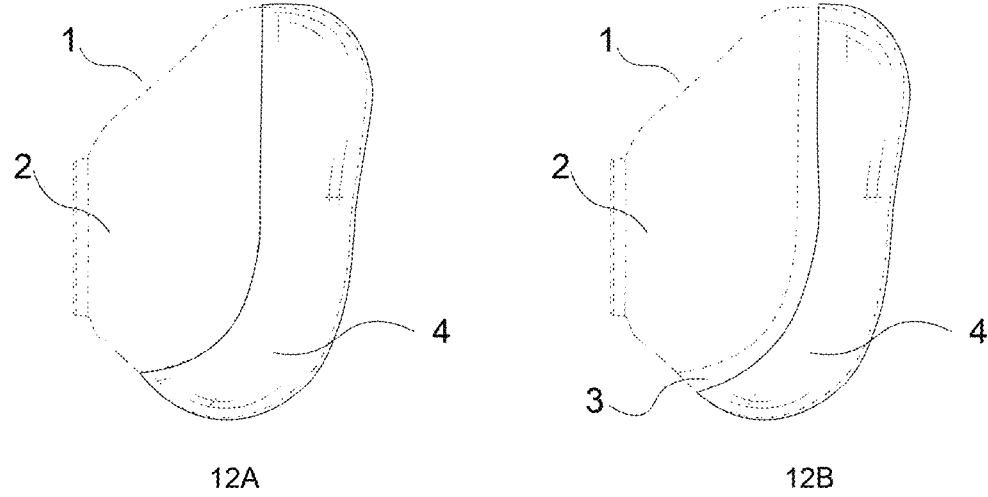
12A                                    12B
Figure 12
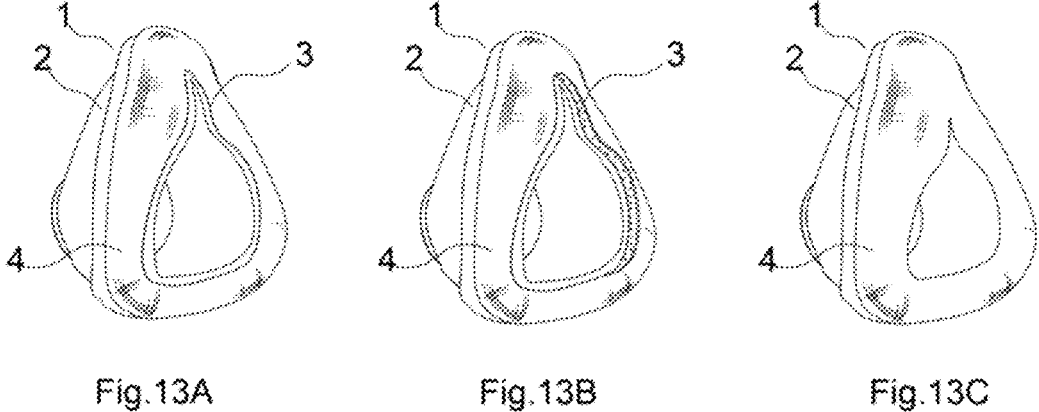
Fig.13A                    Fig.13B                    Fig.13C

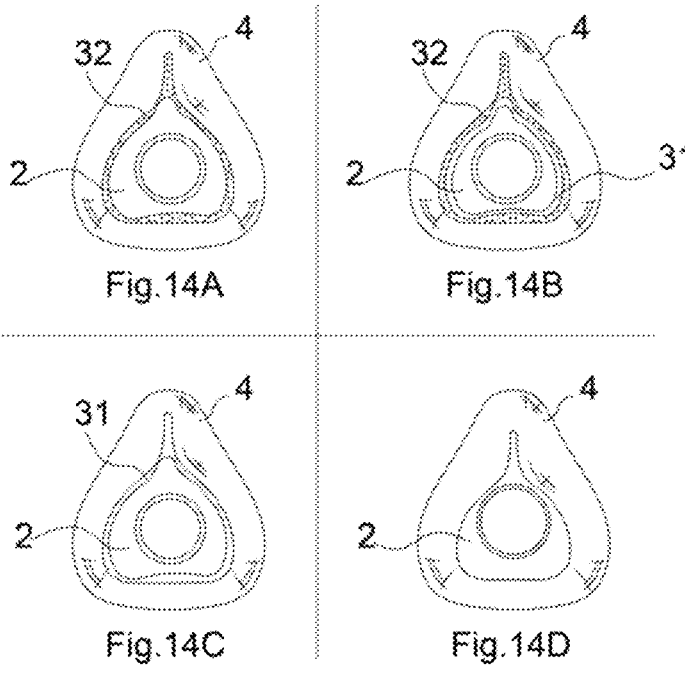
Fig.14A    Fig.14B
Fig.14C    Fig.14D
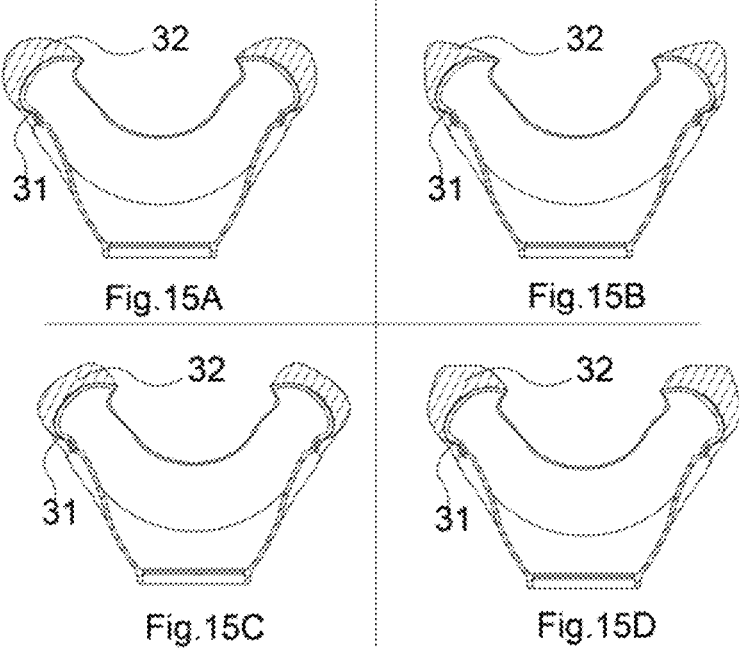
Fig.15A    Fig.15B
Fig.15C    Fig.15D

RESPIRATORY MASK WITH SPONGE AND FABRIC

CROSS REFERENCE

This application is a continuation application of U.S. application Ser. No. 18/509,937, filed on Nov. 15, 2023. The disclosure of the prior application is incorporated by reference.

TECHNICAL FIELD

This disclosure pertains to treatment of one or more breathing-related conditions, using a respiratory mask with a cushioning layer that is able to deform to different facial features of patients or users and a comfort layer that directly contacts the patient's or user's face. The respiratory mask is not only configured to ensure the sealing of the nose and mouth of the user, it provides a comfortable wearing experience.

BACKGROUND

Breathing is one of the crucial processes for sustaining vital functions, and its main purpose is to realize gas exchange through the interplay of the upper and lower respiratory tracts, introducing oxygen from the external environment into the body while expelling carbon dioxide generated by metabolism. However, some people cannot perform normal gas exchange due to the collapse of their airways, failing to inhale sufficient oxygen and exhale carbon dioxide to the lungs, leading to a series of diseases and disorders due to respiratory failure. Obstructive Sleep Apnea (OSA) is a form of sleep-related breathing disorder characterized by the obstruction of the upper airway during sleep. One way to treat OSA is continuous positive air pressure (CPAP) therapy, where patients need to wear the corresponding device connected to a machine providing positive pressure gas, supplying patients with adequate pressurized air for breathing. There are numerous challenges in designing respiratory masks that come in contact with the patients' face, such as, the face having a complex three-dimensional shape, and the head and nose of the patient consisting of bones and soft tissues that vary in structure, size, shape, and sensitivity level from person to person. During sleep, the patient may move, leading to displacement of the respiratory mask, and the sealing area of the mask may consequently change; thus, the design of the respiratory mask needs to consider sealability, comfort of wear, patient adaptability, and flexibility in deformation, allowing a mask to meet different patients' needs to the greatest extent possible.

However, most respiratory masks currently in use typically employ soft materials like silicone or rubber to make contact with and seal against the patient's face. These flexible materials can adequately conform to changes in the patient's facial structure, thus achieving a sealing effect. However, treatments usually take place at night, requiring patients to continuously wear the respiratory mask for 8-16 hours or more. During this time, for physiological reasons, the oils secreted by sebaceous glands or sweat secreted due to lack of air circulation may interact with the non-breathable soft gel materials, potentially leading to the blockage of facial pores, thereby increasing the risk of acne, blackheads, or pressure sores. The mixture of oil and water might make the soft gel materials more prone to shifting relative to the face, leading to slippage or, due to improper positioning, causing irritation or red marks on the skin.

Given the drawbacks of pure silicone respiratory masks, the market has introduced combinations of respiratory masks and mask covers. Most mask covers are made of fabric and are detachable, connecting to and covering the surface of the silicone layer of the mask. The fabric can easily absorb sweat and oil, providing a dry and comfortable environment for the patient's face. However, since there is no fixed part, the mask cover can slide relative to the silicone layer, and the fabric can easily bunch up, making it more difficult for patients to wear the mask and increasing the likelihood of the mask shifting on the patient's face during sleep. Moreover, the full-face respiratory masks with sponge has also been introduced into the market. The sponge is attached to the silicone layer and makes contact with the patient's face. Compared to the previous two masks, the porosity, connectivity, and softness of the sponge ensure that the sponge respiratory masks can absorb oil and sweat while also providing better pressure dispersion. However, since the sponge is typically directly exposed to the external environment, frequent friction or applied pressure can cause the sponge to wear or break, generating small debris, easily leading to skin allergies or inhalation into the patient's airways, shortening the usage cycle of the respiratory mask and causing unnecessary waste.

Hence, there is a need to design a respiratory mask that encompasses both comfort and durability. The contact part should utilize materials that are breathable, soft, skin-friendly, durable, and absorbent. Additionally, the mask should have some adjustable features, allowing it to conform to the patient's face and adapt to deformations. Furthermore, while ensuring the sealing of the patient's respiratory passages, it should provide a comfortable wearing experience, thereby enhancing patient adherence to using the product.

SUMMARY

In view of the above deficiencies, it is necessary to address the aforementioned shortcomings by providing a comfortable respiratory mask that can deform according to different users' facial features and seal the nasal and oral airways of the user.

In an embodiment, a respiratory mask with a sponge and fabric is provided. The respiratory mask with the sponge and fabric is configured to seal and deliver pressurized airflow to an entrance of a user's nasal and oral airways. The respiratory mask includes a partially rigid support chamber having curved sidewalls, the curved sidewalls being connected to form two annular openings, in which the two annular openings include a circular opening configured to be away from a user's face to form a first opening configured to receive pressurized gas, and a symmetrical opening configured to be nearest to the user's face to form a second opening configured to connect with a cushioning part; the cushioning part including an elastic body and a sponge body, the elastic body having a smooth side that, at least in part, is configured to conform to curves of the user's face and a fixed side connected to the support chamber, in which the smooth side and the fixed side are connected by a curved connection, and the sponge body has a curved side configured to face the user's face and a connecting side opposite to the curved side configured to connect with the smooth side of the elastic body; and a comfort layer, including a first side, which is configured to at least partially contact the user's face, and a second side opposite to the first side and configured to connect with the sponge body, in which the comfort layer is configured to be in contact with a nasal bridge of the user
and, together with the cushioning part, is configured to form
a sealing on the user's face, wherein the comfort layer
includes an absorbent material. Only the comfort layer is
configured to contact the user's face and has an inner edge
to accommodate the user's oral and nasal airways, the inner
edge of the comfort layer being smaller than or equal to an
inner edge of the elastic body. Additionally, the cushioning
part and the comfort layer are both configured to deform, in
which degrees of deformation of different parts of the
cushioning part and the comfort layer vary when applying
pressure of the same magnitude to different points on the
cushioning part and the comfort layer in a direction perpen-
dicular to a coronal plane.

In an embodiment, the cushioning part and the comfort
layer correspond to the user's nasal bridge, under the eyes,
and chin, the cushioning part undergoes different deforma-
tions in each area to conform to the user's face, and the
comfort layer adapts with corresponding deformations in
sync with the sponge body during use.

In an embodiment, an inner edge of the sponge body is
larger than or equal to an inner edge of the comfort layer.

In an embodiment, the elastic body has different elastic
moduli in different areas.

In another embodiment, a respiratory mask with a sponge
and fabric is provided. The respiratory mask with sponge
and fabric is configured to seal and deliver pressurized
airflow, e.g., relative to environmental air pressure, to an
entrance of a user's nasal and oral airways. The respiratory
mask includes a partially rigid support chamber having
curved sidewalls, the curved sidewalls being connected to
form two annular openings, in which the two annular
openings include a circular opening configured to be away
from the user's face to form a first opening configured to
receive pressurized gas, and a symmetrical opening config-
ured to be nearest to the user's face to form a second opening
configured to connect with a cushioning part;

the cushioning part including an elastic body and a sponge
body, the elastic body having a smooth side that, at least
in part, is configured to conform to curves of the user's
face and a fixed side connected to the support chamber,
in which the smooth side and the fixed side are con-
nected by a curved connection, and the sponge body
has a curved side configured to face the user's face and
a connecting side opposite to the curved side config-
ured to connect with the smooth side of the elastic
body; and a comfort layer, including a first side, which
is configured to at least partially contact the user's face,
and a second side opposite to the first side and config-
ured to connect non-detachably to the sponge body, in
which the comfort layer, together with the cushioning
part, is configured to form a sealing on the user's face,
the comfort layer including an absorbent material. The
comfort layer has an inner edge configured to accom-
modate the user's oral and nasal airways and at least
partially covers the sponge body, part of an inner edge
of the comfort layer is larger than an edge of the curved
side of the sponge body, and the comfort layer, together
with the sponge body, is configured to form a seal to the
user's airways. Both the cushioning part and the com-
fort layer are configured to deform, and the comfort
layer adapts with corresponding deformations in sync
with the sponge body during use.

In an embodiment, an inner edge of the sponge body is
smaller than or equal to an inner edge of the elastic body.

In an embodiment, the comfort layer and the sponge body
is continuous.

In an embodiment, a shape of an inner edge of the sponge
body is approximately triangular, teardrop-shaped,
V-shaped, or U-shaped.

In yet another embodiment, a respiratory mask with a
sponge and fabric is provided. The respiratory mask with
sponge and fabric is configured to seal and deliver pressur-
ized airflow, e.g., relative to environmental air pressure, to
an entrance of a user's nasal and oral airways. The respira-
tory mask includes a partially rigid support chamber having
curved sidewalls, the curved sidewalls being connected to
form two annular openings, in which the two annular
openings include a circular opening configured to be away
from the user's face to form a first opening configured to
receive pressurized gas, and a symmetrical opening config-
ured to be nearest to the user's face to form a second opening
configured to connect with a cushioning part; the cushioning
part including a sponge body and including a curved side
configured to face the user's face and a connecting side
opposite to the curved side configured to connect with the
second opening of the support chamber; and a comfort layer,
having a first side, which is configured to at least partially
contact the user's face, and a second side opposite to the first
side and configured to connect with the sponge body, in
which the comfort layer is configured to be in contact with
a nasal bridge of the user and, together with the cushioning
part, is configured to form a sealing on the user's face, the
comfort layer including an absorbent material. The sponge
body having one or more of the following characteristics:

a. a thickness of at least 8 mm;

b. a width of at least 8 mm;

c. a density at or between 10 to 200 $kg/m^3$.

In an embodiment, the support chamber has a platform
provided for connecting with the sponge body, and the
sponge body is connected to the platform.

In an embodiment, a connection method between the
sponge body and the platform of the support chamber is
through adhesive, hot melt, welding, molding, or co-mold-
ing.

In an embodiment, the sponge body has different elastic
moduli in different areas.

In another embodiment, a respiratory mask with a sponge
and fabric is also provided. The respiratory mask with
sponge and fabric is configured to seal and deliver pressur-
ized airflow, e.g., relative to environmental air pressure, to
an entrance of a user's nasal and oral airways. The respira-
tory mask includes a partially rigid support chamber having
curved sidewalls, the curved sidewalls being connected to
form two annular openings, in which the two annular
openings include a circular opening configured to be away
from the user's face to form a first opening configured to
receive pressurized gas, and a symmetrical opening config-
ured to be nearest to the user's face to form a second opening
configured to connect with a cushioning part; the cushioning
part including an elastic body and a sponge body, the elastic
body having a smooth side that, at least in part, is configured
to conform to curves of the user's face and a fixed side
connected to the support chamber, in which the smooth side
and the fixed side are connected by a curved connection, and
the sponge body has a curved side configured to face the
user's face and a connecting side opposite to the curved side
configured to connect with the smooth side of the elastic
body; and a comfort layer, including a first side, which is
configured to at least partially contact the user's face, and a
second side opposite to the first side and configured to
connect with the sponge body, in which the comfort layer,
together with the cushioning part, is configured to form a
sealing on the user's face, and the comfort layer including a breathable material. The comfort layer has an inner edge configured to accommodate the user's oral and nasal airways and at least partially covers the sponge body, the inner edge of the comfort layer is larger than an edge of the smooth side of the elastic body, and the comfort layer, together with the sponge body, is configured to form a seal to the user's airways. Both the cushioning part and the comfort layer are configured to deform, and the comfort layer adapts with corresponding deformations in sync with the sponge body during use. The comfort layer has one or more of the following characteristics:

a. a thickness of the comfort layer being at least 0.2 mm;
   b. a surface roughness of the surface of the first side having a Ra value of no less than 0.2;
   c. a surface area ratio of the first side of the comfort layer to the curved side of the sponge body being at or between 0.2 to 5.

In an embodiment, an inner edge of the sponge body is smaller than or equal to an inner edge of the elastic body.

In an embodiment, a material of the comfort layer includes natural or synthetic fibers, and the comfort layer includes a single layer or a multilayer composite.

In an embodiment, a thickness of the comfort layer does not exceed 3.5 mm.

In yet another embodiment, a respiratory mask is provided with a sponge and fabric, which is configured to seal and deliver pressurized airflow, e.g., relative to environmental air pressure, to an entrance of a user's nasal and oral airways. The respiratory mask includes a partially rigid support chamber having curved sidewalls, the curved sidewalls being connected to form two annular openings, in which the two annular openings include a circular opening configured to be away from the user's face to form a first opening configured to receive pressurized gas, and a symmetrical opening configured to be nearest to the user's face to form a second opening configured to connect with a cushioning part; the cushioning part including an elastic body and a sponge body, the elastic body having a smooth side that, at least in part, is configured to conform to curves of the user's face and a fixed side connected to the support chamber, in which the smooth side and the fixed side are connected by a curved connection, and the sponge body has a curved side configured to face the user's face and a connecting side opposite to the curved side configured to connect with the smooth side of the elastic body; and a comfort layer, having a first side, which is configured to at least partially contact the user's face, and a second side opposite to the first side and configured to connect with the sponge body, in which the comfort layer is configured to contact a nasal bridge of the user, and the comfort layer, together with the cushioning part, is configured to form a seal on the user's face, the comfort layer including a breathable material. Only the comfort layer is configured to contact the user's face and has an inner edge configured to accommodate the user's oral and nasal airways, and the inner edge of the comfort layer is smaller than or equal to an inner edge of the elastic body. Both the cushioning part and the comfort layer are configured to deform, in which degrees of deformation at different parts of the cushioning part and the comfort layer vary when applying pressure of the same magnitude to different points on the cushioning part and the comfort layer in a direction perpendicular to a coronal plane.

In an embodiment, an inner edge of the sponge body is larger than or equal to an inner edge of the elastic body.

In an embodiment, the elastic body and the sponge body are connected by molding, foaming, or adhesive, and the sponge body is connected to the comfort layer through adhesive or foaming.

In an embodiment, a cross-sectional shape of the sponge body is triangular, quadrilateral, pentagonal, or hexagonal, and an inner edge of the sponge body is configured to connect with the elastic body.

The respiratory mask with the sponge and the fabric has the following beneficial effects:

1. Enhanced wear comfort and increased stability: Compared to the existing pure silicone respiratory masks, the inclusion of a sponge body and comfort layer, which both offer comfort and breathability, improves the overall feel of using respiratory mask. Fabrics and sponges, with their interstitial spaces and surface tension, can accommodate gas and liquid molecules. When sweat and oils attach to the fabric or sponge surface, the surface tension draws these molecules in. With the sponge body's intricate and extensive pore structure, if the comfort layer becomes saturated, it allows continued flow towards the sponge body, ensuring the user's face remains dry and comfortable throughout the night. This avoids the respiratory mask from shifting relative to the face due to user's sweat or oil secretion.

2. Dispersion of pressure and reduction of pressure marks: The sponge body has elasticity, and its porous structure allows the respiratory mask to expand when faced with external pressure. This helps distribute pressure over a wider area, reducing the sensation of pressure at specific points. Air can circulate through the pores, ensuring the sponge body remains fluffy and doesn't press against the face, also avoiding skin irritations due to lack of breathability. The soft material of the sponge allows the respiratory mask to adapt better to the face's three-dimensional contours. This results in the necessary deformation without inducing pressure, reducing pressure marks induced by the respiratory mask, thus providing a more comfortable user experience.

3. The sponge body exhibits strong anti-wrinkling and shape retention capabilities: The anti-wrinkling capability ensures that, under external forces, the sponge mostly bounces back to its original shape, unlike materials such as paper or fabric that easily crease. Shape retention ensures that the sponge maintains its original form, even under prolonged or sustained external forces, without permanent deformation. The sponge body is softer than the elastic body. By attaching the sponge body to the elastic body, it better offers users a deformable cushioning part. The porous structure of the sponge can adaptively seal against the user's face, minimizing air leaks from partial displacements. When the respiratory mask is removed by the user, the shape-retaining property of the sponge springs into action, reverting the mask to its original state. This counters potential hardening issues experienced with silicone after prolonged use, extending the lifespan of the respiratory mask.

4. Comfort layer enhances the sponge's tear strength: While the sponge body's intricate and vast porous structure makes it soft and breathable, its porous interconnecting structure or interconnecting walls might be overly delicate, leading to potential breakages and shedding, creating sponge debris that could be inhaled by users. The comfort layer adds a protective film to the sponge's surface, maintaining its deformation capabilities, and providing a similarly comfortable and safe contact surface for the user. Additionally, with the comfort layer's robust wear resistance and resilience, instances of surface debris and tearing from the sponge body due to wear are substantially reduced.

5. Improved sealing: Compared to the existing respiratory mask, the respiratory mask as discussed herein with the sponge body and comfort layer enhances user-friendliness. For a subset of users, such as those with beards or facial indentations from injuries, the sponge and comfort layer offer superior softness and deformation capabilities, effectively bridging gaps, like the slight protrusions formed by facial hair. With a singular, molded elastic body in contact with the face, gaps might remain around the beard, compromising the seal of the user interface pad. However, the soft comfort layer and sponge body adapt more seamlessly to facial contours, filling gaps around the beard under facial pressure, ensuring an improved seal. Additionally, their porous structure ensures breathability for users with facial injuries, preventing potential inflammatory symptoms.

6. Modular component compatibility reduces carbon emissions in production: Using a singular mask design as a foundation, modular component production implies a more refined and efficient manufacturing process. Primary components can be meticulously designed to enhance longevity, while supplementary components can be paired based on individual user needs with the main elements, aiding in the reduction of energy consumption and waste during the manufacturing process. By minimizing energy use and waste and promoting recycling of certain components, carbon emissions during production are reduced, contributing to environmental protection.

BRIEF DESCRIPTION OF THE DRAWINGS

FIGS. 7A, 7B, 7C are front views of a platform of the support chamber of the respiratory mask in various configurations according to embodiments and a corresponding cross-sectional view taken in the B-B direction of the platform of the support chamber;

FIGS. 8A and 8B are cross-sectional views taken in the B-B direction from FIGS. 7A, 7B, 7C, showing a comfort layer with different layers;

FIGS. 12A and 12B are three-dimensional schematic views of a respiratory mask according to embodiments;

FIGS. 13A, 13B, 13C are three-dimensional schematic views of a respiratory mask according to embodiments;

FIGS. 14A, 14B, 14C, 14D are front views of a respiratory mask according to embodiments;

FIGS. 15A, 15B, 15C, 15D are cross-sectional views showing a contour shape of a sponge body of a respiratory mask according to embodiments;

DETAILED DESCRIPTION

To make the objectives, features, and advantages of the present disclosure more clear and understandable, the disclosure will be further described in detail with reference to the accompanying drawings. Many specific details are set forth in the following description to provide a thorough understanding of the disclosure. However, the disclosure can be implemented in many ways other than those specifically described here, and those skilled in the art can make similar modifications without deviating from the essence of the disclosure. Therefore, the present disclosure is not limited by the specific embodiments disclosed below.

Unless otherwise defined, all technical and scientific terms used herein have the same meaning as commonly understood by those of ordinary skill in the art of this disclosure. The terms used in this description are intended only for the purpose of describing specific embodiments and are not intended to limit the disclosure.

Figure 16:
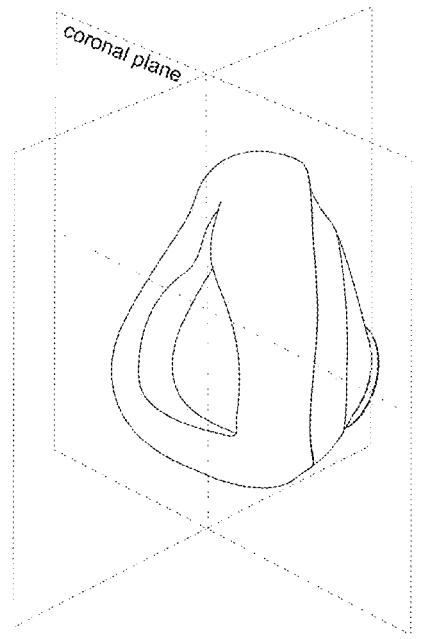
FIG. 16 is a schematic view of a coronal surface of a respiratory mask according to an embodiment.

The present disclosure integrates the comfort layer, sponge body, and a respiratory mask to create a cushioned respiratory mask that is comfortable. The respiratory mask may consist of three main components: the support chamber, the cushioning part, and the comfort layer. The respiratory mask has openings on both sides: one side is configured to receive pressurized gas, while the other side is configured to enclose and seal a user's oral and nasal airways. The upper end of the respiratory mask 1 contacts the user's nasal bridge, while the lower end touches the user's chin, ensuring a sealed connection at least between the nasal bridge and the chin. The areas where the respiratory mask contacts the user's face can be divided into the nasal bridge area 5, under the eyes area 6, and chin area 7. Considering the three-dimensional nature of human facial features, different regions of the cushioning part have varied elastic moduli. When equal pressure is applied to different points of the respiratory mask in a direction perpendicular to the coronal plane (as shown in FIG. 16), different parts of the mask deform differently due to the applied force. The comfort layer is configured to adapt to the deformations created by the sponge body, distributing the force evenly across the user's face, thus enhancing the user's experience when wearing the respiratory mask.

The following will detail several structures of the respiratory mask with the cushioning part and comfort layer, using specific embodiments.

Embodiment 1

The respiratory mask, according to an embodiment, integrated with sponge and fabric, has parts that are configured to extend vertically, passing over the user's nasal bridge, under the eyes, and reaching the chin. They correspond to the nasal bridge area 5, under the eyes area 6, and chin area 7 of the respiratory mask 1, and the mask surrounds the user's oral and nasal entrances (the nose and mouth) to create a sealing area. In essence, the respiratory mask 1 is configured to concurrently cover the user's nose and mouth. By establishing a sealed interface with the user's face, it channels a flow of air that's pressurized relative to the ambient atmosphere into the user's nasal and oral airways, catering to the therapeutic requirements of the user.

Figure 6:
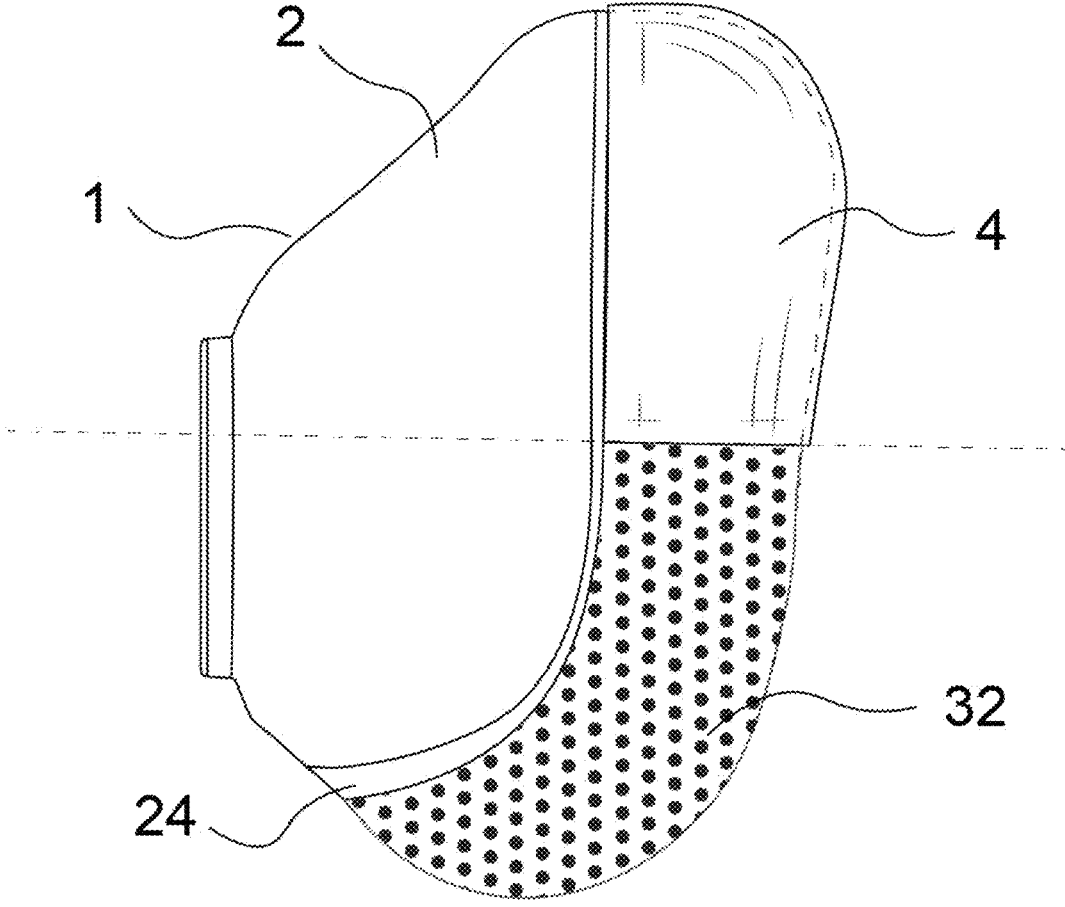
FIG. 6 is a schematic view of a respiratory mask structure according to an embodiment.

For a detailed description, please refer to FIGS. 1 through 4, as well as FIG. 6. This embodiment of the respiratory mask 1 encompasses a support chamber 2, a cushioning part 3, and a comfort layer 4. Specifically, the support chamber 2 integrates a curved sidewall 21 with at least one curvature. The sidewall 21 seamlessly joins to form two annular openings of varied dimensions. The circular opening positioned farther away from the user's face is the first opening 22, while the axially symmetrical opening nearest to the user's face is the second opening 23. The first opening 22 is configured to receive pressurized gas, while the second opening 23 is configured for attachment to the cushioning part 3. When the cushioning part 3 includes a comprehensive elastic body 31 and a sponge body 32, the region around the second opening 23 provides at least two different contact surfaces to connect with the elastic body 31. This ensures that the elastic body 31 firmly connects to the respiratory mask 1, mitigating the risks of cracks or insufficient connections. The material for at least part of the partially rigid (in order to maintain the support chamber 2 for supporting the cushioning part 3 or to ensure the stable transmission of pressurized gas, such as by connecting and supporting a portion of the cushioning part 3; or receiving the pressurized gas through the first opening 22) support chamber 2 can be high-density polyethylene, polypropylene, polycarbonate, or similar materials manufactured through injection molding. The support chamber 2 can also incorporate noise reduction materials or a small section made of neutral materials with a hardness lesser than the rigid part. The neutral section materials can be polyester, acrylic, and the like, while the noise reduction materials can be nylon, cotton, natural fabrics, and so on. The thickness of the sidewall 21 is at or between 1 to 5 mm, guaranteeing the support chamber 2 retains ample sturdiness to link the cushioning part 3 and to receive the pressurized gas. Generally, the sidewall 21 presents a consistent and even structure. Still, it might also incorporate a few through-holes or be fitted with a noise-reducing mesh (configured to dispel the exhaled waste gas from the user). The sidewalls 21 could have protrusions or grooves serving as positioning or anchoring mechanisms (for aligning or securing other components) or parts with other functional roles. The size and contour of the first opening 22 are typically dictated by the adjoining elbow, conduit, or support structure that channels the pressurized gas. Usually, it is perceived as a circular opening with a diameter at or between 10 to 45 mm. The extended wall thickness stemming from the first opening may be either equal to the thickness of the sidewall 21 or be slightly thinner. The shape and scale of the second opening 23 are determined by the cushioning part 3 that connects with the second opening 23. The shape of the second opening 23 is usually symmetrical, with the second opening 23 larger than the first opening 22.

The cushioning part 3 may consist of an elastic body 31 and a sponge body 32. The elastic body 31 includes a smooth side 311 that conforms, at least in part, to the curvature of the user's face, and a fixed side 312 that connects to the support chamber 2. The smooth side 311 and the fixed side 312 are linked through a curved connection. The purpose of the elastic body 31 is to provide attachment points for the sponge body 32. These attachment points can be on the surface or cross-sectional surface. Together, the elastic body 31 and the sponge body 32 form the complete cushioning part 3. Notably, at least a portion of the surface of the smooth side 311 may not lie on a singular plane. The elastic body 31 has variable elastic moduli in different areas. For instance, in the nasal bridge area 5, it has a relatively thinner wall thickness and the elastic modulus is directly proportional to wall thickness. This allows the elastic body 31 in the nasal bridge area 5 to exhibit greater deformability, ensuring a snug fit of the respiratory mask 1 against the skin, and adjusts to the three-dimensional pressures applied by the facial contours and is inherently soft, allowing it to adapt to any facial morphological changes. Its material composition may include rubber, silicone, or elastic plastic, and it can be connected to the support chamber 2 through molding or integral formation. For instance, the surface of the smooth side 311 may undergo polishing to eradicate minuscule imperfections, enhancing its smoothness. The surface roughness of the smooth side 311 and the fixed side 312 can be the same or different. For example, the surface of the smooth side 311 can be polished to eliminate small irregularities, improving smoothness and providing a better touch to the face. The surface of the fixed side 312 can be textured to increase its friction, ensuring a tighter connection between the elastic body 31 and the support chamber 2. The inner side of the curved connection can be reinforced with ribs, or the wall thickness of the elastic portion can be single-layered or multi-layered. This is to prevent the respiratory mask 1 from being too thin and potentially bursting or blowing open. Additionally, the region of the elastic body 31 corresponding to the under the eyes area has protruding wing pieces 311A crafted to closely fit against the sidewalls on either side of the nasal bridge. The sponge body 32 includes a curved side 321 that faces the user's face and a connecting side 322 opposite to the curved side 321. The connecting side 322 is configured to connect to the smooth side 311 of the elastic body 31. The sponge body 32 serves as a linkage to the elastic body 31 and also provides attachment points for the comfort layer 4. Together, the elastic body 31, sponge body 32, and comfort layer 4 make up the deformable sealing portion of the respiratory mask 1. Furthermore, the sponge body 32 possesses properties of adsorption, breathability, and noise reduction. The sponge body 32 has a curved contour to ensure a tight seal on the user's face and to fit with the support chamber 2 or the elastic body 31. The shape of the sponge body 32 can be either continuous or discontinuous; a continuous annular sponge can directly adhere to the surface of the elastic body 31. The connecting side 322 can be either flat or curved, and its softness and deformability ensure the sponge body 32 adapts to any deformations at the joint. The sponge body 32 may have a non-uniform thickness, with the thickest parts being at least 0.5 mm, to guarantee ample deformability and breathability. The thickness diminishes gradually from the center towards the inner and outer edges, creating a gradient thickness. This allows the sponge body 32 to smoothly adhere to the elastic body 31, avoiding any step-offs that might leave impressions on the user's face. Alternatively, it can also maintain a uniform thickness to ensure that, once the sponge body 32 is connected to the elastic body 31, the cushioning part 3 will conform comfortably and smoothly to the user's face.

In terms of material composition, the sponge may possess characteristics such as disinfection resistance, breathability, water absorption, and biocompatibility (ensuring no allergic or other adverse reactions when in contact with human skin). The cross-sectional shape of the sponge body 32 can be triangular, quadrilateral, pentagonal, hexagonal, or any other shape that conforms to the contours of the face. As shown in FIG. 15, FIG. 15A displays an arc shape, FIG. 15B depicts a triangular shape, FIG. 15C illustrates a quadrilateral shape, and FIG. 15D presents a pentagonal shape (with rounded corners). Potential materials include medical-grade polyurethane sponge (known for its excellent biocompatibility, lightweight softness, and hypoallergenic properties), medical waxy sponge (effective for liquid absorption and suitable for wound dressings and hemostatic purposes), polyether sponge (offering superior elasticity and durability), and polyester sponge (light and soft). The sponge body 32 is adhered to the elastic body 31 using adhesive. When choosing the adhesive material, several key factors may be taken into account: 1) Bonding strength: It may be important for the adhesive to effectively bond different types of materials and tissues. The bond should be robust and long-lasting, ensuring that no relative displacement or detachment occurs under external forces. This bond should remain consistent even in conditions exposed to body fluids such as sweat and oils; 2) Material properties: Important characteristics to consider include biocompatibility, non-toxicity (ensuring it doesn't release harmful substances or gases), biodegradability, antimicrobial properties, usability (with appropriate viscosity and fluidity for ease of application), and rapid curing; 3) Appearance and odor: The adhesive should not emit any irritating or unpleasant smells. When considering the color, opt for hues that provide comfort to ensure a pleasant experience for the user; 4) Environmental considerations: It may be ideal for the adhesive to contain a low amount of volatile organic compounds (VOCs). Generally, water-based or solvent-free formulations are preferable as they minimize the chances of emissions into the air, reducing potential negative impacts on both patient health and air quality.

The comfort layer 4 includes a first side 41 that at least partially comes into contact with the user's face and an opposite second side 42. The material for the comfort layer 4 can be absorbent or breathable, such as fabric or other comfortable textiles, like fleece. It boasts the advantages of being moisture-wicking and highly breathable, effectively absorbing the secretions from a user's face during the night, ensuring the face remains dry and well-ventilated, thus enhancing user adherence to the use of the respiratory mask 1. To ensure the comfort layer 4 possesses superior durability and resistance against tearing or wear, its thickness should be at least 0.2 mm but no more than 3.5 mm. The material for the comfort layer 4 can be one or a combination of natural fabrics or synthetic fibers such as cotton (soft and breathable), silk elastic fabric, wool, spandex, polyester elastic fiber, polyester fiber (wrinkle-resistant, wear-resistant), nylon fiber (high strength, wear-resistant), elastane (excellent elasticity, durable), and polypropylene fiber (lightweight, wear-resistant). Some sections of the comfort layer 4 can also be made in conjunction with metal fibers to produce specialized comfort layers, such as antibacterial or anti-static fabrics. Given that the permeation rate of the respiratory mask 1 should be less than 20 L/min, the breathability of the comfort layer 4 also has specific requirements. It needs to be comfortable for the wearer without allowing excessive gas leakage. According to the ASTM D737-18 air permeability test method, the air permeability of parts of the comfort layer 4 should be at or between 1 to 30 CFM. In another embodiment, the air permeability rate is approximately 40-60 CFM, or it can be 50-80 CFM. The comfort layer 4 also needs to absorb the sweat from the user's face, so there are specific requirements for its moisture absorption properties. According to the AATCC 79-2018 test method, the absorption time for part of the comfort layer 4 should be less than 30 seconds, with a preferred absorption time of less than 20 seconds and an even more optimal time of less than 10 seconds. Besides its absorptive function, the primary role of the comfort layer 4 is to enhance the tear strength of the sponge, preventing the sponge from tearing or shedding particles. The connection state between the sponge body 32 and the comfort layer 4 can be such that the comfort layer 4 fully contacts the curved side 321 of the sponge body 32. Since the comfort layer 4 comes into contact with the user's face, the Ra (surface roughness) value of the first side 41 that contacts the face can be particularly important. This is to avoid situations where an overly rough surface might scratch the user's face. The surface roughness of different materials may vary due to the material properties, manufacturing processes, and other factors. Thus, the range for the Ra value should be at or between 0.2 to 10 micrometers. The inner edge shape of the fabric for the comfort layer 4 can be triangular, oval, gourd-shaped, teardrop-shaped, or other shapes that can enclose the oral and nasal airways. The outer edge can be shaped according to the support chamber 2, sponge body 32, or elastic body 31, and it can either match or differ from the shape of the inner edge. The formation of the comfort layer 4 can be achieved through methods like cutting, laser cutting, line cutting, water jet cutting, or CNC cutting, as long as the desired shape is attained.

Figures 17A, 17B, 17C:
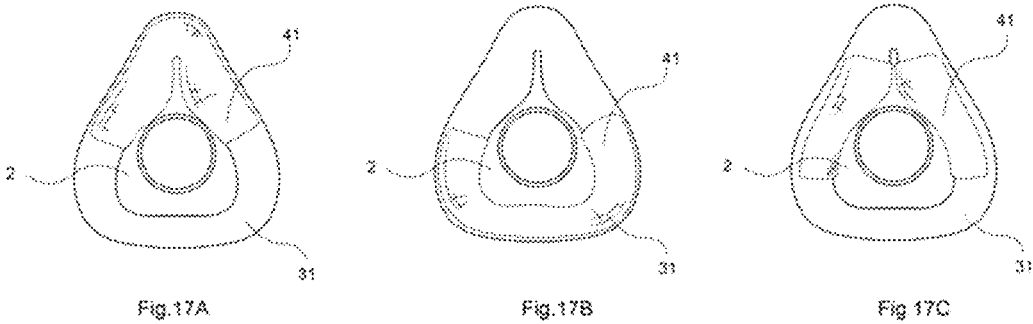
FIGS. 17A, 17B, 17C are schematic views of a comfort layer in different configurations of a respiratory mask according to embodiments.

The method of bonding the comfort layer 4 to the sponge body 32 can include the use of glue, heat sealing, pressure bonding, sewing, pressing, laser welding. Alternatively, the comfort layer 4 can be connected to the sponge through a material (such as thermoplastic polyurethane, etc.) that is distinct from the material of the comfort layer 4 and the sponge body 32. To ensure the quality and performance of the bond, several factors may be taken into consideration: 1) Material selection: Choosing the right bonding materials ensures compatibility and prevents delamination or failure to adhere during the process; 2) Pre-treatment: Before bonding, the surfaces of the materials should be clean, free from oil, dust, wrinkles, or any other contaminants that could affect the user's experience; 3) Characteristics: The chosen bonding method should take into account its properties, like ensuring adhesives are non-toxic and compatible. For heat sealing or pressing, the temperature and pressure applied should not damage or deform the materials; 4) Environmental considerations: Regardless of the method chosen, energy conservation, waste management, and process optimization should be thoroughly considered. After the sponge body 32 and the comfort layer 4 are combined, the comfort layer 4 should flexibly adapts with any deformation in sync with the sponge body 32. The comfort layer 4 can be either continuous (connecting end to end to form an annular shape) or non-continuous (forming a shape that is not end-to-end connected as shown in FIGS. 17A, 17B, 17C). The surface area ratio between the first side 41 of the comfort layer 4 and the curved side 321 of the sponge body is at or between 0.2 to 5. This ensures that the comfort layer 4 and sponge body 32 can provide sensitive protection to different areas as per the user's requirements. The comfort layer 4 at least partially comes into contact with the user's nasal bridge, and the area of contact with the nasal bridge can be at or between 1 to 5 square millimeters. The perimeter of the inner edge of the comfort layer 4 should be no less than 126 mm, ensuring it can comfortably house the user's mouth and nose airways.

The combination of the elastic body 31, sponge body 32, and comfort layer 4 forms a seal on the user's face. This is to address the issues presented by most existing respiratory masks 1 that use silicone or similar non-breathable materials to fit the user's face. Due to prolonged wear and pressure, the user's face may develop red marks, pressure sores during use, or, for physiological reasons, the face might sweat or produce oil. This can cause the non-breathable and non-absorbent silicone pad to lose friction against the user's face, leading to issues like the respiratory mask 1 slipping or becoming misaligned. This, in turn, can weaken the overall seal of the mask, diminishing its therapeutic effectiveness. However, fabrics and sponges, with their interstitial spaces and surface tension, can accommodate gas and liquid molecules. When sweat and oils adhere to the surface of the fabric or sponge, their surface tension draws the gas and liquid molecules in, ensuring that the user's face remains dry and comfortable throughout the night. This also helps prevent the respiratory mask 1 from shifting due to the sweat or oils secreted by the user. Moreover, with the sponge's inherent elasticity and softness, it can quickly adjust and conform to the unique three-dimensional features of various user's faces when in contact. Therefore, this disclosure incorporates materials that offer comfort, breathability, and elasticity. The highly adaptable elastic body 31 and sponge body 32 are set as the cushioning part 3, allowing respiratory mask 1 to buffer and adapt to the user's facial contours. By adding the breathable comfort layer 4, it not only enhances the overall user experience of the respiratory mask 1 but also ensures its sealing efficiency.

Referring back to FIGS. 1 to 4, the comfort layer 4 has an annular contour (with a continuous shape where the beginning and end meet). The comfort layer 4 contacts the nasal bridge and inner edge of the comfort layer 4 is smaller than that of the elastic body 31, while the inner edge of the sponge body 32 is larger than that of the elastic body 31. The cushioning part 3 and comfort layer 4 correspond to the user's nasal bridge, below the eyes, and chin. Furthermore, the cushioning part 3 can deform to fit the user's face, while the comfort layer 4 adapts with the deformations of the sponge body 32 in sync (e.g., when the comfort layer 4 changes, the corresponding deformation occurs in the sponge body 32.) To enhance the deformability of the cushioning part 3, the elastic body 31 of the cushioning part 3 has different elastic moduli in different areas (by adjusting the wall thickness, the number of layers, or by adding support ribs). In the direction perpendicular to the coronal plane, when equal pressure is applied to different points on the cushioning part 3 and the comfort layer 4, the cushioning part 3 and the comfort layer 4 deform to different degrees at different locations. For instance, when the sponge body 32 has a uniform thickness, applying the same pressure in the same direction results in similar deformation at any location on the sponge body 32, meaning that the degrees of deformation (distance of deformation) is the same. In this case, the sponge body 32 and the comfort layer 4 conform to the deformation of the elastic body 31. That is, when pressure is applied to points where the elastic modulus of the elastic body 31 is smaller, the degree of deformation (distance of deformation) of the cushioning part 3 and the comfort layer 4 is less than at points where the elastic modulus of the elastic body 31 is greater. In situations where the sponge body 32 has a non-uniform thickness, in order to provide a better comfort experience for the patient, a recess corresponding to the user's nasal bridge is created in the nasal bridge area 5. In other words, the nasal bridge area 5, which corresponds to the user's nasal bridge, is thinner in the elastic body 31 and the sponge body 32. When the same pressure is applied to the respiratory mask 1 in the same direction, the degree of deformation (distance of deformation) of the cushioning part 3 and the comfort layer 4 at the points in the nasal bridge area 5 where force is applied is greater than at other points.

Figure 1:
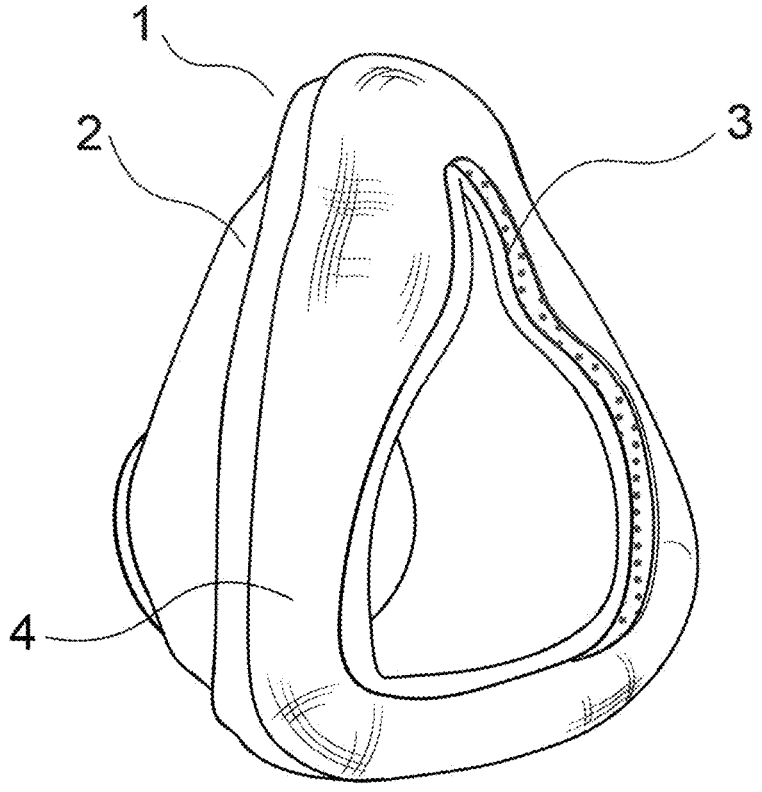
FIG. 1 is the schematic view of a respiratory mask structure according to an embodiment.
Figure 2:
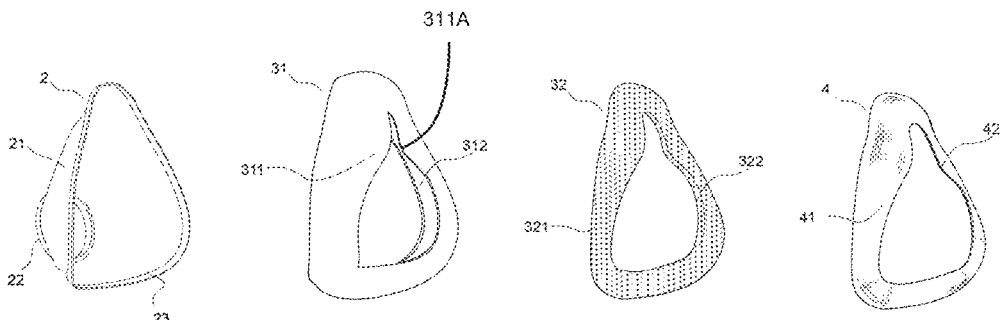
FIG. 2 is the exploded view of a respiratory mask structure according to an embodiment.
Figure 3:
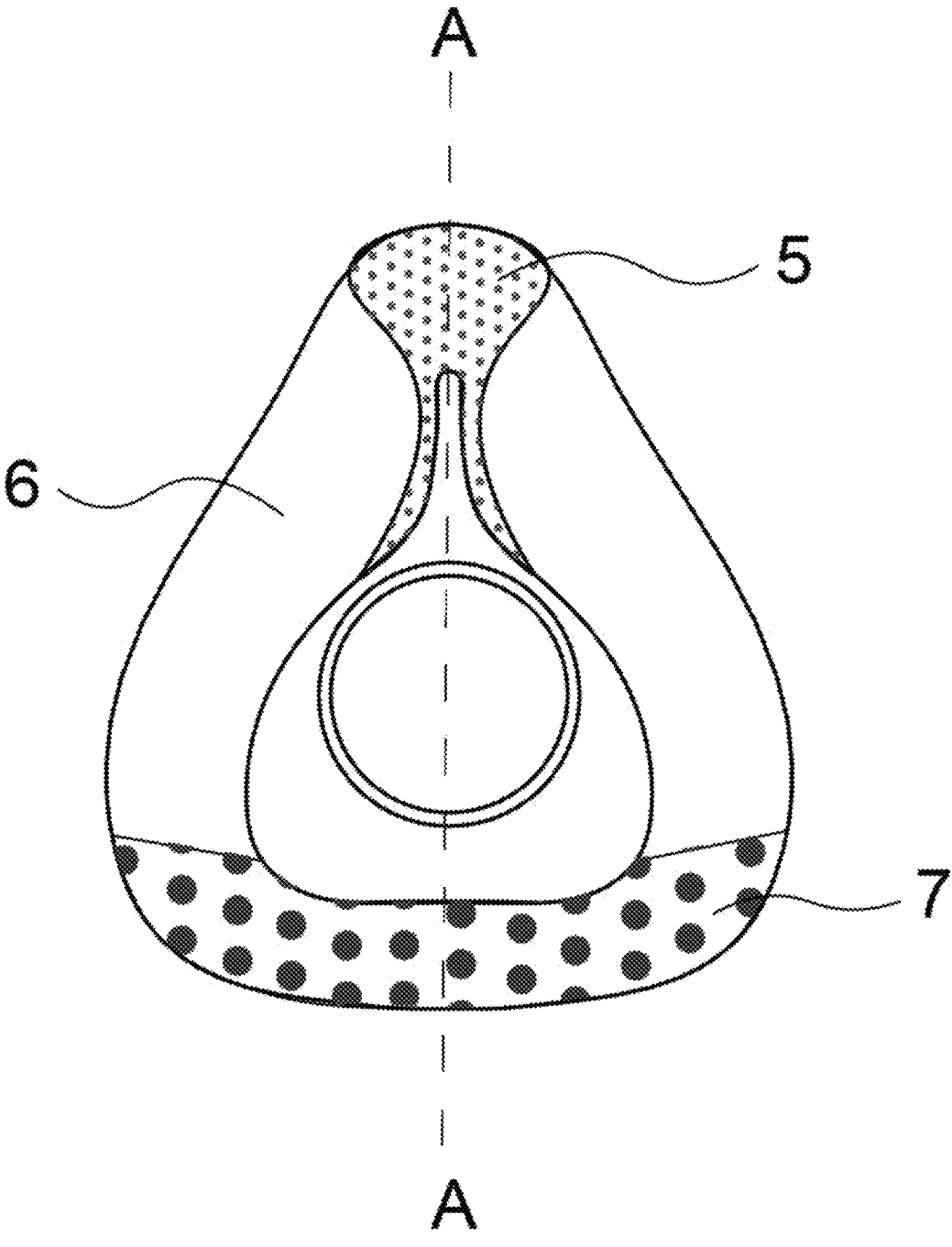
FIG. 3 is a rear view of a respiratory mask according to an embodiment.
Figure 4:
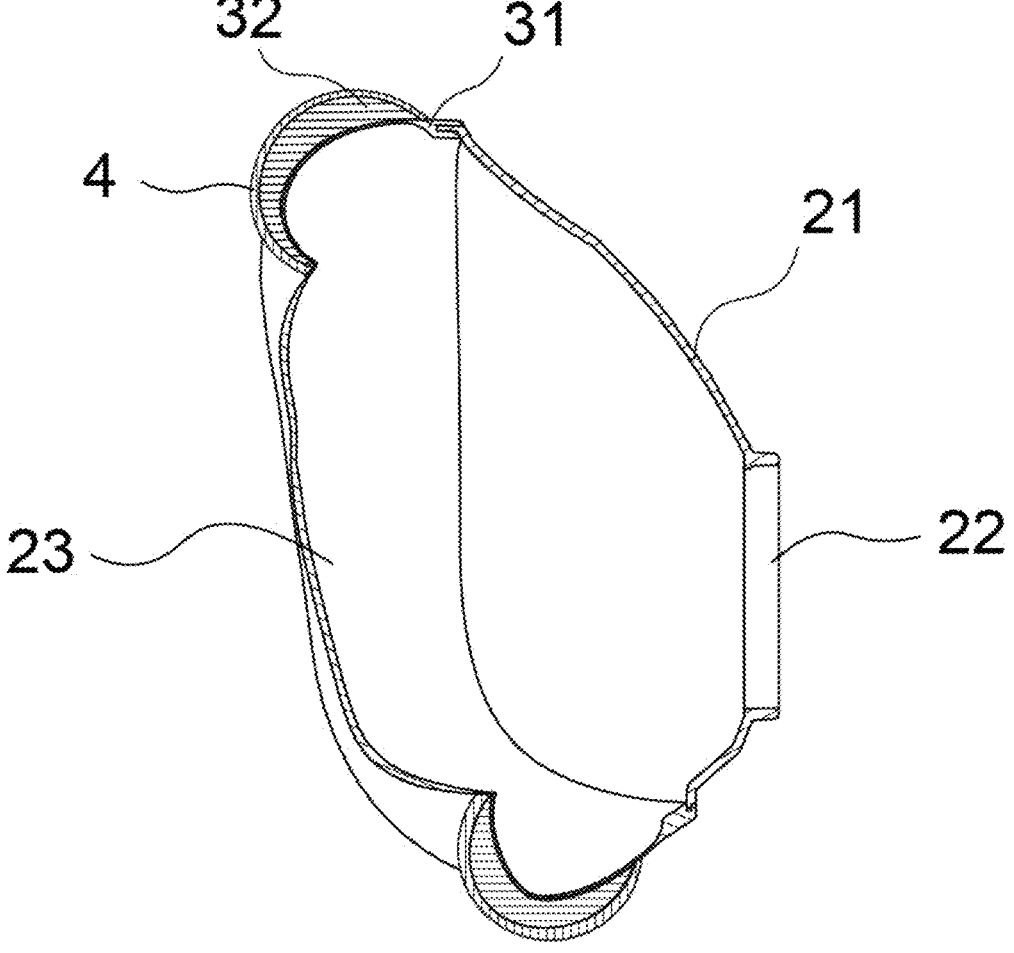
FIG. 4 is a cross-sectional view taken in the A-A direction from FIG. 3.
Figure 5:
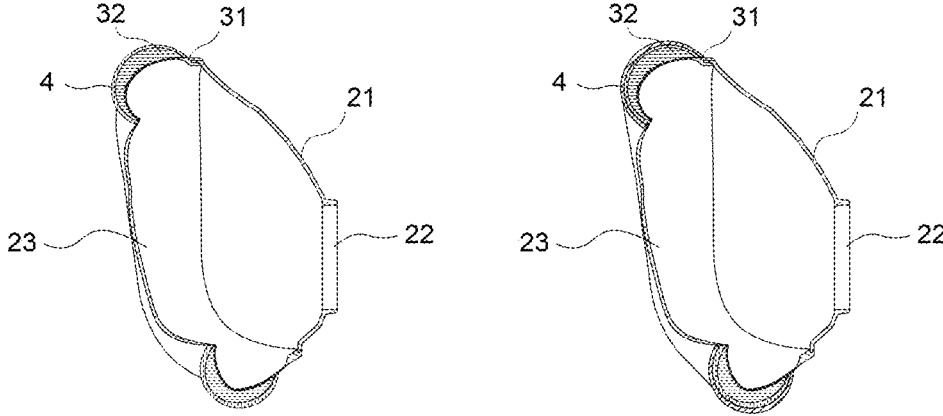
FIG. 5 is a cross-sectional view taken in the A-A direction from FIG. 3, showing the comfort layer with different layers.

Referring to FIG. 5, to satisfy the varying softness and functional needs of different user groups during use, the comfort layer 4 in the respiratory mask 1 can be multi-layered (formed from the same material or different materials stacked in two or more layers as shown in FIG. 5B). In this disclosure, the material of the comfort layer 4 can be one or more types of natural fabrics or synthetic materials and can be compounded in multiple layers to achieve a soft and fluffy texture. This way, when a user's face contacts the respiratory mask 1 during wear, not only does the cushioning part 3 provide sealing adjustments, but the multi-layered comfort layer 4 also offers certain modulations to achieve optimal sealing. The material of the comfort layer 4 in this disclosure can also include metal fibers or other materials that can be compounded to have functions beyond just comfort. When a user uses this multi-layered compound comfort layer 4, the respiratory mask 1 can offer antibacterial, antistatic, or thermoregulating effects.

Referring to FIG. 13, the range where the outer edge of the comfort layer 4 contacts the elastic body 31 can vary. As shown in FIG. 12A, in this embodiment, the outer edge of the comfort layer 4 can be connected to the elastic body 31. As shown in FIG. 12B, in this embodiment, the outer edge of the comfort layer 4 can be connected to where the elastic body 31 meets the support chamber 2, wrapping the outer edge of the sponge body 32 within the comfort layer 4. This can prevent the edge of the sponge body 32 from easily getting damaged, thereby extending the lifespan of the respiratory mask 1.

Embodiment 2

In this embodiment, the respiratory mask, integrated with sponge and fabric, has parts that are configured to extend vertically, passing over the user's nasal bridge, under the eyes, and reaching the chin. They correspond to the nasal bridge area 5, under the eyes area 6, and chin area 7 of the respiratory mask 1, and the mask surrounds the user's oral and nasal entrances (the nose and mouth) to create a sealing area, delivering airflow at a pressure higher than the ambient atmospheric pressure to the user's nasal and oral airways. The respiratory mask includes a support chamber 2, a cushioning part 3, and a comfort layer 4. The difference between the respiratory mask 1 provided in this embodiment and the one in embodiment 1 is that the cushioning part 3 consists solely of the sponge body 32. As shown in FIGS. 6-7C, in this embodiment, the sponge body 32 is directly connected to the support chamber 2. Specifically, as depicted in FIG. 6 (a side view showing the sponge body 32 directly connected to the platform 24 of the support chamber 2, with the portion above the horizontal line showing the comfort layer 4 attached to the sponge body 32 and the part below the horizontal line revealing the connection of sponge body 31 with the platform 24 of the support chamber 2, omitting the comfort layer 4), the second opening 23 of the support chamber 2 is configured to connect with the sponge body 32. A platform 24 is provided at the second opening 23 to connect with the sponge body 32. This platform 24 can extend inwards and outwards from the second opening 23 (referring to FIG. 7C) or only inwards or only outwards (referring to 7A for extending outwards and 7B for extending inwards). The perimeter of the inner edge of the platform 24 should not be less than 114.5 mm to ensure a stable connection with the sponge body 32 and that the sealing scope encloses both the nasal and oral airways.

The sponge body 32 includes a curved side 321 facing the user's face and an opposite connecting side 322. The connecting side 322 is designed to connect with the second opening 23 of the support chamber 2. The thickness of the sponge body 32 is at least 8 mm, and its width is also at least 8 mm. This ensures that the cushioning structure has ample volume for compressive deformation. The density range of the sponge body 32 is at or between 10 to 200 kg/m³. A too-high density can lead to increased hardness and weight of the sponge, reducing its deformability and water-absorption ability. Conversely, a too-low density may result in insufficient elasticity and decreased water absorption. The connection between the sponge body 32 and the platform 24 of the support chamber 2 can be achieved through methods like adhesive bonding, hot melting, welding, molding, co-molding or other non-detachable means. The comfort layer 4 is connected to the curved side 321 of the sponge body 32 and can deform in response to changes in the sponge's shape. The complete sponge cushioning layer makes the respiratory mask 1 softer, more breathable, and with fewer types of materials, making it more environmentally friendly.

Referring to FIG. 8, to meet the needs for softness and functionality for different users during use, the comfort layer 4 in the respiratory mask 1 can be multi-layered (referring to 8A). The material of the comfort layer 4 in this disclosure can be one or multiple types of natural fabrics or synthetic materials and can be layered to achieve a soft and fluffy texture. This way, when a user's face comes in contact with the respiratory mask 1 during wear, aside from the cushioning part 3 providing a sealing adjustment, the multi-layered comfort layer 4 can also offer some adjustments to achieve optimal sealing. The materials for the comfort layer 4 in this disclosure can also include metal fibers and other such materials that, in addition to comfort, offer added functionalities. When users use this multi-layered composite comfort layer 4, the respiratory mask 1 can offer antibacterial, anti-static, or temperature-regulating effects.

Embodiment 3

Figure 9:
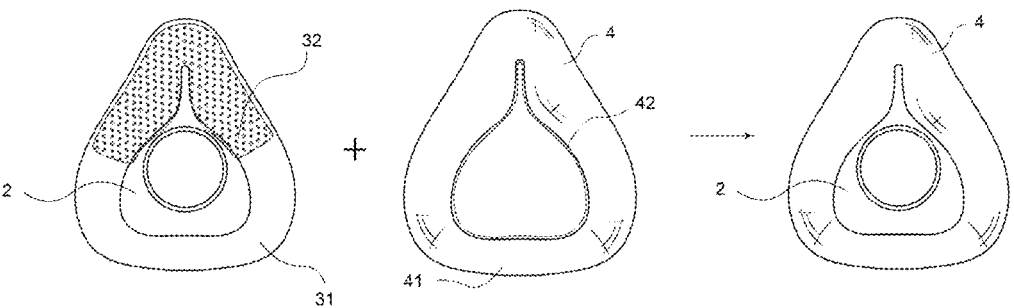
FIG. 9 is a schematic view of an inverted V-shaped sponge body of a respiratory mask according to an embodiment.

In this embodiment, the respiratory mask, integrated with sponge and fabric, has parts that are configured to extend vertically, passing over the user's nasal bridge, under the eyes, and reaching the chin. They correspond to the nasal bridge area 5, under the eyes area 6, and chin area 7 of the respiratory mask 1, and the mask surrounds the user's oral and nasal entrances (the nose and mouth) to create a sealing area, delivering a pressurized airflow relative to the ambient air pressure into the user's nasal and oral airways. The respiratory mask may consist of the support chamber 2, cushioning part 3, and comfort layer 4. The difference between the respiratory mask 1 in this embodiment and the one in embodiment 1 lies in the coverage area of the sponge body 32. As shown in FIG. 9, in this embodiment, the sponge body 32 is non-annular (not connected at the start and end). Specifically, the sponge body 32 has an inverted V-shape. The topmost part seals the nasal bridge, the bottommost part is no lower than below the eyes, and it connects to the elastic body 31. The sponge body 32 can have variable thickness and different elastic moduli in different areas. When connected, the bottommost part smoothly connects with the elastic body 31, without forming a noticeable step. The comfort layer 4 partially adheres to the sponge body 32 and partially to the elastic body 31. The inverted V-shaped sponge body 32 and the elastic body 31 together constitute the cushioning part 3 of the respiratory mask 1, providing a more comfortable sealing environment for the nasal bridge. This avoids the pressure on the nasal bridge that may result from the sealing of a single elastic body 31. Furthermore, materials that are comfortable and breathable are used in areas like the nasal bridge area and under the eyes area, which tend to produce oils. This is designed to absorb the oils and sweat generated by users during wear, reducing relative displacement. This enhancement is aimed at improving the overall user experience of the respiratory mask 1.

Figure 10:
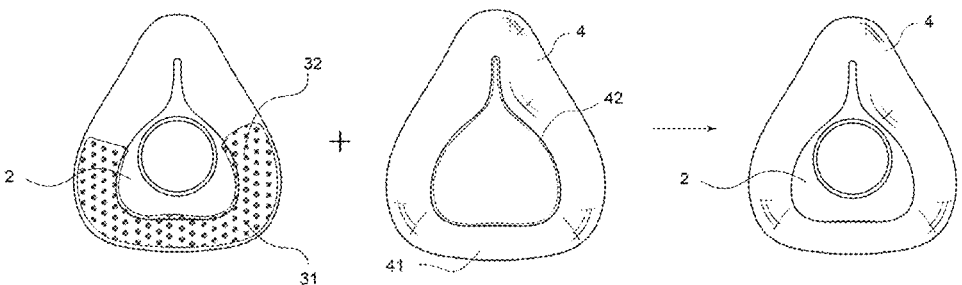
FIG. 10 is a schematic view of a U-shaped sponge body of a respiratory mask according to an embodiment.
Figure 11:
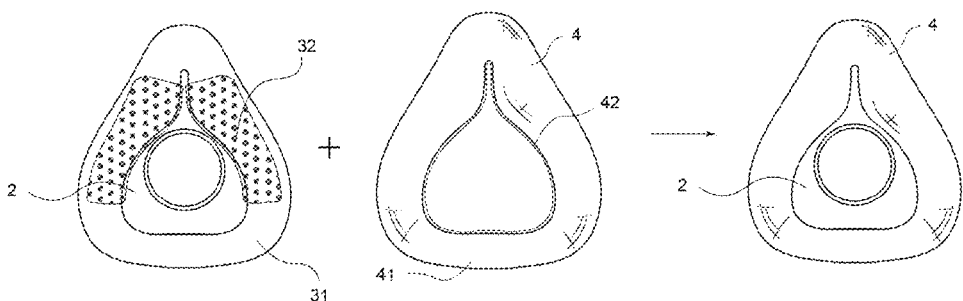
FIG. 11 is a schematic view of a regional sponge body of a respiratory mask according to an embodiment.

In this embodiment, there may be two implementations: First, as shown in FIG. 10, the sponge body 32 takes on a U-shape. Its topmost point does not extend beyond under the eyes, while its bottommost part seals the chin area 7 and connects with the elastic body 31. The sponge body 32 can exhibit variable thickness and different elastic moduli in various sections. When connected, the uppermost part transitions smoothly with the elastic body 31, avoiding any noticeable steps. The comfort layer 4 partially adheres to the sponge body 32 and partially to the elastic body 31. Together, the U-shaped sponge and the elastic body 31 form the cushioning part 3 of the respiratory mask 1. This design offers enhanced sealing for the chin, preventing the issues that might arise if a single elastic body 31 couldn't fully conform to the contour of the user's chin, leading to reduced airtightness. Second, as illustrated in FIG. 11, the sponge body 32 has a certain curvature. Its topmost point does not go beyond below the eyes and connects with the elastic body 31. The sponge body 32 can have varying thicknesses and different elastic moduli in different areas. When connected with the elastic body 31, both the uppermost and bottommost points transition smoothly with the elastic body 31 without any obvious steps. The comfort layer 4 partly adheres to the sponge body 32 and partly to the elastic body 31. The sponge body 32, in conjunction with the elastic body 31, forms the cushioning part 3 of the respiratory mask 1. This design provides better sealing for users with facial traumas or indentations.

Embodiment 4

In this embodiment, the respiratory mask, integrated with sponge and fabric, has parts that are configured to extend vertically, passing over the user's nasal bridge, under the eyes, and reaching the chin. They correspond to the nasal bridge area 5, under the eyes area 6, and chin area 7 of the respiratory mask 1, and the mask surrounds the user's oral and nasal entrances (the nose and mouth) to create a sealing area, delivering airflow pressurized relative to the ambient atmospheric pressure to the user's nasal and oral airways. The respiratory mask includes a support chamber 2, a cushioning part 3, and a comfort layer 4. The distinctive feature of the respiratory mask 1 in this embodiment compared to that in Embodiment 1 is the range the inner edge of the comfort layer 4 contacts the user's face. As depicted in FIGS. 13A and 14C, when the inner edge of the comfort layer 4 is larger than the inner edge of the elastic body 31 but smaller than the inner edge of the sponge body 32, and the inner edge of the sponge body 32 is smaller than the inner edge of the elastic body 31, the comfort layer 4 and the elastic body 31 jointly make contact with the user's face (e.g., when in use, both the comfort layer 4 and the elastic body 31 come into contact with the patient's face). As shown in FIGS. 13B and 14C, when the inner edge of the comfort layer 4 equals the inner edge of the sponge body 32 and is larger than the inner edge of the elastic body 31, both the comfort layer 4 and the elastic body 31 come into contact with the user's face. As illustrated in FIGS. 13C and 14D, when the inner edge of the comfort layer 4 is smaller than the inner edge of the elastic body 31, only the comfort layer 4 contacts the user's face. By wrapping the outer edge of the sponge body 32 inside the comfort layer 4, potential damages to the edges of the sponge body 32 can be prevented, extending the lifespan of the respiratory mask 1. Additionally, it avoids issues where certain users might have allergic reactions or skin sensitivity to the sponge, preventing potential discomfort when using the respiratory mask 1.

In another implementation, different contact surfaces are provided to meet varying needs of the user. As shown in FIG. 14A, the inner edge of the comfort layer 4 is larger than that of the sponge body 32, and the inner edge of the sponge body 32 is equal to the inner edge of the elastic body 31. The comfort layer 4, together with the sponge body 32, is configured to jointly make contact with the user's face. In FIG. 14B, the inner edge of the comfort layer 4 is larger than that of the sponge body 32, and the inner edge of the sponge body 32 is larger than that of the elastic body 31. In this case, the comfort layer 4, sponge body 32, and elastic body 31 collectively make contact with the user's face.

Additionally, the technical features mentioned in these embodiments above can be combined as needed to produce a respiratory mask 1 that includes all or some of these technical features. The respiratory mask 1 with sponge and fabric in accordance with this disclosure has at least the following beneficial effects:

1. Enhanced wear comfort and increased stability: Compared to the existing pure silicone respiratory masks, the inclusion of a sponge body and comfort layer, which both offer comfort and breathability, improves the overall feel of using respiratory mask. Fabrics and sponges, with their interstitial spaces and surface tension, can accommodate gas and liquid molecules. When sweat and oils attach to the fabric or sponge surface, the surface tension draws these molecules in. With the sponge body's intricate and extensive pore structure, if the comfort layer becomes saturated, it allows continued flow towards the sponge body, ensuring the user's face remains dry and comfortable throughout the night. This avoids the respiratory mask from shifting relative to the face due to user's sweat or oil secretion.

2. Dispersion of pressure and reduction of pressure marks: The sponge body has elasticity, and its porous structure allows the respiratory mask to expand when faced with external pressure. This helps distribute pressure over a wider area, reducing the sensation of pressure at specific points. Air can circulate through the pores, ensuring the sponge body remains fluffy and doesn't press against the face, also avoiding skin irritations due to lack of breathability. The soft material of the sponge allows the respiratory mask to adapt better to the face's three-dimensional contours. This results in the necessary deformation without inducing pressure, reducing pressure marks induced by the respiratory mask, thus providing a more comfortable user experience.

3. The sponge body exhibits strong anti-wrinkling and shape retention capabilities: The anti-wrinkling capability ensures that, under external forces, the sponge mostly bounces back to its original shape, unlike materials such as paper or fabric that easily crease. Shape retention ensures that the sponge maintains its original form, even under prolonged or sustained external forces, without permanent deformation. The sponge body is softer than the elastic body. By attaching the sponge body to the elastic body, it better offers users a deformable cushioning part. The porous structure of the sponge can adaptively seal against the user's face, minimizing air leaks from partial displacements. When the respiratory mask is removed by the user, the shape-retaining property of the sponge springs into action, reverting the mask to its original state. This counters potential hardening issues experienced with silicone after prolonged use, extending the lifespan of the respiratory mask.

4. Comfort layer enhances the sponge's tear strength: While the sponge body's intricate and vast porous structure makes it soft and breathable, its porous interconnecting structure or interconnecting walls might be overly delicate, leading to potential breakages and shedding, creating sponge debris that could be inhaled by users. The comfort layer adds a protective film to the sponge's surface, maintaining its deformation capabilities, and providing a similarly comfortable and safe contact surface for the user. Additionally, with the comfort layer's robust wear resistance and resilience, instances of surface debris and tearing from the sponge body due to wear are substantially reduced.

5. Improved sealing: Compared to the existing respiratory mask, the version with the sponge body and comfort layer enhances user-friendliness. For a subset of users, such as those with beards or facial indentations from injuries, the sponge and comfort layer offer superior softness and deformation capabilities, effectively bridging gaps, like the slight protrusions formed by facial hair. With a singular, molded elastic body in contact with the face, gaps might remain around the beard, compromising the seal of the user interface pad. However, the soft comfort layer and sponge body adapt more seamlessly to facial contours, filling gaps around the beard under facial pressure, ensuring an improved seal. Additionally, their porous structure ensures breathability for users with facial injuries, preventing potential inflammatory symptoms.

6. Modular component compatibility reduces carbon emissions in production: Using a singular mask design as a foundation, modular component production implies a more refined and efficient manufacturing process. Primary components can be meticulously designed to enhance longevity, while supplementary components can be paired based on individual user needs with the main elements, aiding in the reduction of energy consumption and waste during the manufacturing process. By minimizing energy use and waste and promoting recycling of certain components, carbon emissions during production are reduced, contributing to environmental protection.

The technical features mentioned in the above embodiments can be combined in any manner. To keep the description concise, not all possible combinations of the technical features in the aforementioned embodiments have been detailed. However, as long as these combinations do not conflict, they should be considered within the scope of this disclosure.

The embodiments described above only represent a few possible implementations of the disclosure and are detailed and specific. This should not be interpreted as limiting the scope of the patent. It should be noted that for those skilled in the art, various modifications and improvements can be made without departing from the concept of the disclosure, and these all fall within the protection scope of this disclosure. Therefore, the protective scope of this patent should be defined by the attached claims.

The invention claimed is:

1. A respiratory mask with a sponge and fabric, configured to seal and deliver pressurized gas to an entrance of nasal and oral airways of a user, comprising:

a support chamber having curved sidewalls, the curved sidewalls being connected to form two annular openings, wherein the two annular openings include a first opening and a second opening, wherein the first opening is configured to be away from a face of the user and receive the pressurized gas, and wherein the second opening is configured to be nearer to the face of the user and connect to a cushioning part;

the cushioning part comprising a sponge body, the sponge body having an inner edge;

a comfort layer comprising a first side and a second side, wherein the first side is configured to at least partially contact the face of the user, wherein the second side is configured to be opposite to the first side, and wherein the comfort layer, together with the cushioning part, is configured to form a sealing on the face of the user;

wherein the comfort layer is configured to contact the face of the user and has an inner edge, wherein the comfort layer and the sponge body are configured to both jointly make contact with the face of the user, and wherein the comfort layer and the sponge body are configured to make contact with the face of the user along a connection between the inner edge of the comfort layer and the inner edge of the sponge body; and wherein both the cushioning part and the comfort layer are configured to deform and the comfort layer adapts with corresponding deformations in sync with the sponge body during use, wherein degrees of deformation of different parts of the cushioning part and the comfort layer vary when applying pressure of a same magnitude to different points on the cushioning part and the comfort layer in a direction perpendicular to a coronal plane.

2. The respiratory mask according to claim 1, wherein a platform is provided at the second opening to connect to the sponge body, and the platform is configured to extend inwards and outwards from the second opening or only inwards or only outwards.

3. The respiratory mask according to claim 2, wherein the platform has an inner edge, and a perimeter of the inner edge of the platform is no less than 114.5 mm.

4. The respiratory mask according to claim 1, wherein the cushioning part further comprises an elastic body.

5. The respiratory mask according to claim 4, wherein the sponge body comprises a curved side configured to face the face of the user and a connecting side opposite to the curved side, the curved side being configured to connect to a smooth side of the elastic body.

6. A respiratory mask with a sponge and fabric, configured to seal and deliver pressurized gas to an entrance of nasal and oral airways of a user, comprising:

a support chamber having curved sidewalls, the curved sidewalls being connected to form two annular openings, wherein the two annular openings include a first opening and a second opening, wherein the first opening is configured to be away from a face of the user and receive the pressurized gas, and wherein the second opening is configured to be nearer to the face of the user and connect to a cushioning part;

the cushioning part comprising a sponge body, the sponge body having an inner edge;

a comfort layer comprising a first side and a second side, wherein the first side is configured to at least partially contact the face of the user, wherein the second side is configured to be opposite to the first side and connect non-detachably to the cushioning part, wherein the comfort layer, together with the cushioning part, is configured to form a sealing on the face of the user;

wherein the cushioning part further comprises an elastic body, the elastic body having a smooth side and a fixed side, wherein the smooth side, at least in part, is configured to conform to curves of the face of the user, wherein the fixed side is connectable to the support chamber, wherein the sponge body is configured to connect to the smooth side of the elastic body;

wherein the comfort layer has an inner edge, the comfort layer and the sponge body are configured to both jointly make contact with the face of the user, and wherein the comfort layer and the sponge body are configured to make contact with the face of the user along a connection between the inner edge of the comfort layer and an inner edge of the sponge body; and wherein both the cushioning part and the comfort layer are configured to deform, and the comfort layer adapts with corresponding deformations in sync with the sponge body during use.

7. The respiratory mask according to claim 6, wherein the elastic body further comprises protruding wing pieces configured to fit against nasal sidewalls.

8. The respiratory mask according to claim 6, wherein a shape of the sponge body is continuous.

9. The respiratory mask according to claim 6, wherein a shape of the sponge body is discontinuous.

10. A respiratory mask with a sponge and fabric, configured to seal and deliver pressurized gas to an entrance of nasal and oral airways of a user, comprising:

a support chamber having curved sidewalls, the curved sidewalls being connected to form two annular openings, wherein the two annular openings include a first opening and a second opening, wherein the first opening is configured to be away from a face of the user and receive the pressurized gas, and wherein the second opening is configured to be nearer to the face of the user and connect to a cushioning part;

the cushioning part comprising a sponge body, the sponge body having an inner edge and being configured to connect to the second opening of the support chamber;

a comfort layer comprising a first side and a second side, wherein the first side is configured to at least partially contact the face of the user, wherein the second side is configured to be opposite to the first side, and wherein the comfort layer, together with the cushioning part, is configured to form a sealing on the face of the user, the comfort layer including an absorbent material;

wherein the comfort layer and the sponge body are configured to both jointly make contact with the face of the user, and wherein the comfort layer and the sponge body are configured to make contact with the face of the user along a connection between an inner edge of the comfort layer and the inner edge of the sponge body;

wherein both the cushioning part and the comfort layer are configured to deform, and the comfort layer adapts with corresponding deformations in sync with the sponge body during use.

11. The respiratory mask according to claim 10, wherein the cushioning part further comprises an elastic body.

12. The respiratory mask according to claim 10, wherein a shape of the sponge body is continuous.

13. The respiratory mask according to claim 10, wherein a shape of the sponge body is discontinuous.

14. The respiratory mask according to claim 10, wherein air permeability of the comfort layer is between 1 CFM and 80 CFM.

15. A respiratory mask with a sponge and fabric, configured to seal and deliver pressurized gas to an entrance of nasal and oral airways of a user, comprising:

a support chamber having curved sidewalls, the curved sidewalls being connected to form two annular openings, wherein the two annular openings include a first opening and a second opening, wherein the first opening is configured to be away from a face of the user and receive the pressurized gas, and wherein the second opening is configured to be nearer to the face of the user and connect to a cushioning part;

the cushioning part comprising a sponge body, the sponge body having an inner edge;

wherein the cushioning part further comprises an elastic body, the elastic body having a smooth side and a fixed side, wherein the smooth side, at least in part, is configured to conform to curves of the face of the user, wherein the fixed side is connectable to the support chamber, wherein the sponge body is configured to connect to the smooth side of the elastic body;

a comfort layer comprising a first side and a second side, wherein the first side is configured to at least partially contact the face of the user, wherein the second side is configured to be opposite to the first side, and wherein the comfort layer, together with the cushioning part, is configured to form a sealing on the face of the user, the comfort layer including a breathable material;

wherein the comfort layer has an inner edge, and the comfort layer and the sponge body are configured to both jointly make contact with the face of the user, and wherein the comfort layer and the sponge body are configured to make contact with the face of the user along a connection between the inner edge of the comfort layer and an inner edge of the sponge body;

wherein both the cushioning part and the comfort layer are configured to deform, and the comfort layer adapts with corresponding deformations in sync with the sponge body during use; and wherein the comfort layer has one or more of the following characteristics:

a perimeter of the inner edge of the comfort layer being no less than 126 mm; and a thickness of the comfort layer being at least 0.2 mm.

16. The respiratory mask according to claim 15, wherein a material of the comfort layer comprises natural or synthetic fibers, and the comfort layer includes a single layer or a multi-layer composite.

17. The respiratory mask according to claim 15, wherein a thickness of the comfort layer does not exceed 3.5 mm.

18. The respiratory mask according to claim 15, wherein the elastic body and the sponge body are connectable by molding, foaming, or adhesive, and the sponge body is connectable to the comfort layer through adhesive or foaming.

19. The respiratory mask according to claim 15, wherein an outer edge of the comfort layer is connected to the elastic body.

20. The respiratory mask according to claim 15, wherein an outer edge of the comfort layer is connected to a connection between the elastic body and the support chamber, such that the comfort layer wraps around an outer edge of the sponge body within the comfort layer.

\* \* \* \* \*